United States Patent [19]

Jones et al.

[11] Patent Number: 4,575,557
[45] Date of Patent: Mar. 11, 1986

[54] PREPARATION OF SUBSTITUTED BENZAMIDES

[75] Inventors: John D. Jones, Bury; David Schofield, Greater Manchester, both of England

[73] Assignee: Imperial Chemical Industries PLC, London, England

[21] Appl. No.: 635,595

[22] Filed: Jul. 30, 1984

[30] Foreign Application Priority Data

Sep. 22, 1983 [GB] United Kingdom ............... 8325408

[51] Int. Cl.⁴ .................. C07D 319/18; C07C 121/78
[52] U.S. Cl. .................................. 549/366; 549/436; 558/392
[58] Field of Search ................... 260/465 D; 549/366, 549/436

[56] References Cited

FOREIGN PATENT DOCUMENTS 0059536 9/1982 European Pat. Off. .

OTHER PUBLICATIONS

Stevens et al, J. Org. Chem. (1953) 18 1112–1116.
Convreur et al, J. Org. Chem. (1953) 501–506.

*Primary Examiner*—Dolph H. Torrence
*Attorney, Agent, or Firm*—Cushman, Darby & Cushman

[57] ABSTRACT

Benzamides of the formula (I):

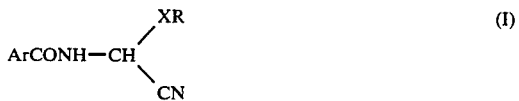

(I)

in which Ar is optionally substituted aryl; X is O, S or NH and R is optionally substituted alkyl or alkenyl when X is O or S, or is optionally substituted alkenoyl when X is NH, are prepared by (a) reacting a compound of the formula (II):

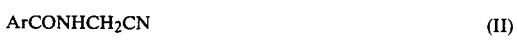

(II)

with a brominating agent in a solvent which is substantially chemically inert to the reactants and in which compound (II) is soluble, to form a compound of the formula (III):

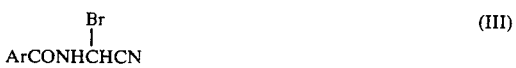

(III)

and (b) reacting the compound (III) with a compound RXH.

Preferably, bromination is carried out rapidly in dried ethyl acetate.

The process avoids hydration of the CN group of the compound (III) to a carbamoyl group obviating a subsequent dehydration step later.

The intermediate compound (III) is novel.

The substituted benzamides are useful as herbicides and fungicides.

1 Claim, No Drawings

PREPARATION OF SUBSTITUTED BENZAMIDES

This invention relates to a process for the preparation of substituted benzamide derivatives useful as herbicides and fungicides, and to novel chemical intermediates used therein.

Substituted benzamide derivatives of the formula (A):

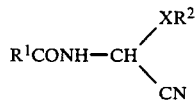

in which $R^1$ is aryl, X is O, S or NH and $R^2$ is optionally substituted alkyl or alkenyl when X is O or S, or optionally substituted alkanoyl when X is NH, and which are proposed for use as herbicides and fungicides, are described in European Patent Specification No. 59536 together with processes for their preparation. One such process involves a sequence of chemical reactions in the following scheme:

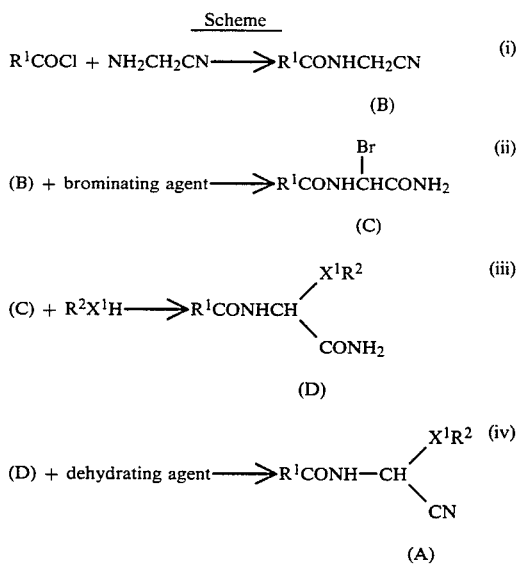

In step (i) of the scheme, an acid chloride $R^1COCl$ is reacted with aminoacetonitrile by a conventional procedure to obtain the acylaminoacetonitrile derivative (B). This is then reacted in step (ii) with a brominating agent (for example bromine in glacial acetic acid) to give the brominated derivative (C). This bromination procedure also simultaneously hydrates the cyano group to a carbamoyl group —$CONH_2$ necessitating treatment with a dehydrating agent later, step (iv), to convert the carbamoyl group back into a cyano group. In step (iii), the bromo compound (C) is reacted with an appropriate alcohol, thiol, or amine of formula $R^2X^1H$ to obtain the carbamoyl compound (D) which is then treated with the dehydrating agent in step (iv) to convert it to the corresponding cyano compound (A).

It is speculated that it may be possible to avoid the undesired conversion of the cyano group to carbamoyl by use of a different solvent of brominating agent and thereby shorten the proces by making step (iv) unnecessary. The present invention is concerned with this aspect.

According to the present invention there is provided a process for the preparation of a substituted benzamide derivative of the formula (I):

in which Ar is optionally substituted aryl; X is O, S or NH and R is optionally substituted alkyl or alkenyl when X is O or S, or is optionally substituted alkenoyl when X is NH, which comprises the steps of (a) reacting a compound of the formula (II):

with a brominating agent in a solvent which is substantially chemically inert to the reactants and in which compound (II) is soluble, to form a compound of the formula (III):

and (b) reacting the compound (III) with a compound RXH, in which R and X have the meanings hereinbefore defined. The invention also includes steps (a) and (b) individually and the novel intermediate compounds of formula (III).

Compounds of formula (II), which are used as starting materials in the process of the invention, may be readily obtained by reacting an acid chloride, ArCOCl, with aminoacetonitrile in known manner.

The optionally substituted aryl group Ar may be a phenyl or naphthyl radical. Examples of substituents which may be present include halogen, viz. fluorine, chlorine, bromine, iodine, $C_1$-$C_4$ alkoxy, methylenedioxy and ethylenedioxy, $C_1$-$C_4$ alkyl, $C_1$-$C_4$ alkylthio, $C_1$-$C_4$ haloalkyl (e.g. $CF_3$) nitro and cyano. There may be from one to three or more substituents which may be the same or different. When Ar is a substituted phenyl radical the substituents are preferably in the 3, 4 or 5 positions. When a methylenedioxy or ethylenedioxy substituent is present, it is preferably attached to the 3 and 4 positions of the phenyl ring. A halogen substituent (e.g. Cl or Br) may also be present in the 4- or 5-position, or both, in such compounds.

The solvent used in the process of the invention may be any solvent which does not react with bromine and which dissolves compound II. Generally, it will be an aprotic solvent and preferably a chlorinated hydrocarbon or an organic nitrile or, especially, an organic ester. Mixtures of solvents may also be used. Examples of suitable solvents are dichloromethane, acetonitrile, and esters of saturated carboxylic acids, particularly those esters of the formula $R^3COOR^4$ in which $R^3$ is $C_{1-4}$ straight or branched chain alkyl, especially methyl, and $R^4$ is $C_{1-6}$ straight or branched chain alkyl e.g. methyl, ethyl, iso-propyl, n-butyl and iso-amyl. Ethyl acetate is favoured. It is desirable to use dried solvents to prevent hydrolysis and maximise product yield.

Bromine is the preferred brominating agent. The reaction with bromine is preferably carried out quickly as the intermediate compound (III) is unstable, but, particularly on a commercial scale, it may prove more practicable to operate a slower bromination and accept a lower yield. Typically a small amount of a solution of bromine in part of the solvent is added to a solution of compound (I) in the bulk of the solvent at room temperature. When the orange colour imparted to the solution by the bromine disappears after a few minutes, the remainder of the bromine solution is added very rapidly, over a matter of seconds, with vigorous agitation. The initiation of the bromination reaction as witnessed by the decolourisation of solution can be speeded up considerably by the addition of a few drops of an acid such as phosphorus tribromide. Almost immediately, step (b) is commenced.

In step (b) the bromo compound (III) is reacted with an appropriate alcohol, thiol or amide of the formula RXH to obtain the desired product (I). When RXH is an alcohol or thiol, R is optionally substituted alkyl or alkenyl, for example $C_{1-4}$ alkyl and $C_{3-5}$ alkenyl optionally substituted with halogen or $C_{1-4}$ alkoxy. When RXH is an amide, R is optionally substituted alkanoyl, preferably, $C_{1-4}$ alkanoyl, for example, formyl, acetyl or propionyl.

The alcohol, thiol or amide should be added rapidly, typically over a matter of seconds, and normally in the presence of a base to remove hydrogen bromide as it is formed during reaction. Tertiary amines, such as triethylamine and pyridine, are suitable bases. The base is used in at least stoichiometric amount, and is added altogether or in part with the alcohol, thiol or amide, the remainder being added afterwards, or possibly, all is added afterwards. It should not, however, be added in advance of the alcohol, thiol or amide as it attacks the nitrile, compound (III). If an amide is used, this may, itself, act as a feeble base and the quantity used in step (b) to permit complete reaction may need to be adjusted accordingly.

Conveniently, a solution of the alcohol, thiol or amide and most of the base in a small amount of the same or different solvent used in step (a), is added rapidly (for instance over 10 to 20 seconds for a preparation on a scale of 0.04 mole) to the reaction mixture from step (a) at a temperature maintained, preferably, below 40° C. Further base is subsequently added to neutralise the reaction mixture.

At the end of reaction, the bromide salt may be removed with water, and the product, compound (I), isolated from the separated organic layer by distilling off the solvent and purified by recrystallisation from, for example, a toluene/methylcyclohexane solution.

The invention is illustrated by the following Examples 1 to 13.

EXAMPLE 1

Preparation of 4-chlorobenzoylamino(ethoxy)acetonitrile via 4-chlorobenzoylamino(bromo)acetonitrile 4-Chlorobenzoylaminoacetonitrile (7.78 g, 0.04 mole) was dissolved in ethyl acetate (125 ml) at 40° C. with stirring and the solution cooled to 25° C. A few drops of a solution of bromine (6.4 g, 0.04 mole) in ethyl acetate (10 ml) were added imparting an orange colour to the nitrile solution. The whole was stirred at 25° C. until decolourisation occurred, which took about 4 to 5 minutes. Upon decolourisation, the remainder of the bromine solution was added very rapidly (about 5 seconds) with vigorous stirring. Immediately following this a solution of absolute ethanol (10 ml) and triethylamine (10 ml) in ethyl acetate (10 ml) was added, the reaction mixture being kept below 40° C. with the aid of a water bath. The addition took about 10 to 20 seconds and was accompanied by a precipitation of triethylammonium bromide which made the solution very thick and difficult to stir efficiently. More triethylamine (about 2 ml) was added dropwise until the reaction mixture, which was pale yellow in colour, was neutralised.

Water (50 ml) was added and the mixture stirred for a few seconds giving an orange organic layer and a colourless aqueous layer. The organic layer was separated and washed with water (2×50 ml) and then boiled with sodium sulphate and carbon and filtered to give a yellow solution. This solution was evaporated under reduced pressure to give a yellow to orange oil which set solid on standing.

The solid was triturated with a 20% toluene/80% methylcyclohexane solution and the very pale yellow solid so obtained was filtered, washed with a 20/80 toluene/methylcyclohexane solution and dried to give 6.0 g of the product, m.p. 102°–105° C. (Yield 62.9%).

The IR spectrum of the product was identical to that of an authentic sample.

EXAMPLE 2

Preparation of 4-chlorobenzoylamino(methoxy)acetonitrile via 4-chlorobenzoylamino(bromo)acetonitrile 4-Chlorobenzoylaminoacetonitrile (3.9 g, 0.02 mole) was dissolved in ethyl acetate at 40° C. with stirring and the solution cooled to 25° C. A few drops of a bromine solution (3.2 g, 0.02 mole) in ethyl acetate (10 ml) was added and the reaction mixture stirred at 25° C. until it decolourised after about 4 minutes. The remaining bromine solution was added rapidly (about 5 seconds) followed immediately by the addition of a solution of methanol (10 ml) and triethylamine (5 ml) in ethyl acetate (10 ml). The reaction mixture was neutralised with further drops of triethylamine and washed with water (3×25 ml). The evaporated organic layer was dried over sodium sulphate, treated with carbon, filtered and the solvent removed by evaporation under reduced pressure. The yellow oil so obtained was dissolved in methanol (50 ml) for analysis by HPLC, after which 3 g of crude product (83%) was isolated and recrystallised from a 50:50 toluene/methylcyclohexane solution to give 2.0 g of the product, m.p. 124°–125° C.

¹Hnmr analysis was consistent with the product having the formula:

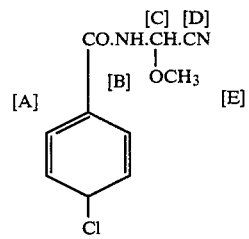

| | A | B | + | C | D | E |
|---|---|---|---|---|---|---|
| Shift ( ) | 7.38–7.81 (m) | | | 7.32 (d) | 6.13 (d) | 3.5 (s) |
| Protons | 2.1 | 3 | | | 1 | 3 |

[s = singlet; d = doublet; m = multiplet]

EXAMPLE 3

Preparation of 4-methylbenzoylamino(ethoxy)acetonitrile via 4-methylbenzoylamino(bromo)acetonitrile 4-Methylbenzoylaminoacetonitrile (3.48 g, 0.02 mole) was dissolved in dried ethyl acetate (70 ml) at 40° C. with stirring and the solution cooled to 30° C. A few drops of a bromine solution (3.2 g, 0.02 mole) in dried ethyl acetate were added and the remaining bromine solution was added rapidly (about 5 seconds) followed immediately by the addition of absolute ethanol (10 ml). The reaction mixture was neutralised by the addition of triethylamine. The triethylamine hydrobromide was filtered and washed with ethyl acetate (2×20 ml). The filtrate was treated with a decolourising carbon and water (20 ml) added. The mixture was stirred for 10 minutes, filtered and the ethyl acetate removed from the filtrate under reduced pressure to leave an off-white solid which was recrystallised from an acetone/water mixture. The white crystalline product was dried at 70° C. Yield=2.7 g (62%), mp=136°-142° C.

'Hnmr analysis was consistent with the product having the formula:

$$H_3C-\text{C}_6H_4-CONHCH(CN)(OC_2H_5)$$

EXAMPLE 4

Preparation of 4-chlorobenzoylamino(ethoxy)acetonitrile via 4-chlorobenzoylamino(bromo)acetonitrile by a slower bromination procedure 4-Chlorobenzoylaminoacetonitrile (19.45 g, 0.1 mole) was dissolved in dried ethyl acetate (300 ml) with stirring at 25° C. and treated with a few drops of a bromine solution (12.0 g, 0.015 mole) in dried ethyl acetate (10 ml) and stirred at 25° C. until decolourised (about 4 minutes). The remainder of the bromine solution was added over a period of 10 minutes and the reaction mixture was stirred for 30 minutes and filtered with absolute ethanol (50 ml). The filtrate was neutralised with 2,6-dimethylpyridine and the 2,6-dimethylpyridine hydrobromide was filtered and washed with ethyl acetate (2×25 ml). The filtrate was treated with water (25 ml) and the ethyl acetate was stripped off under reduced pressure to leave a yellow solid in water. The solid was filtered, dissolved in acetone (100 ml), and water (30 ml) and a decolourising carbon (2 g) were added. The mixture was stirred at 20° C. for 15 minutes and filtered. The acetone was stripped off the filtrate under reduced pressure to leave a very pale yellow solid in water which was filtered and dried at 50° C. Yield=55% based on 4-chlorobenzoylaminoacetonitrile, 74% based on bromine; m.p.=109°-112° C.

The IR spectrum of the product was identical to that of an authentic sample of 4-chlorobenzoylaminoacetonitrile.

EXAMPLE 5

Preparation of 4-chlorobenzoylamino(ethoxy)acetonitrile in alternative solvents 4-chlorobenzoylamino(ethoxy)acetonitrile was prepared in similar fashion except that different solvents to ethyl acetate were used. The solvent and yield of product are tabulated below.

| Example | Solvent | Yield % |
| --- | --- | --- |
| 5 | Methyl acetate | 27 |
| 6 | Iso-propyl acetate | 39 |
| 7 | Iso-amyl acetate | 17 |
| 8 | n-Butyl acetate | 19 |
| 9 | Acetonitrile | 13 |
| 10 | Ethyl acetate/acetonitrile [2:1] | 39 |
| 11 | Dichloromethane | 44 |

EXAMPLE 12

Isolation of the bromonitrile intermediate, 4-chlorobenzoylamino(bromo)acetonitrile (IV)

4-Chlorobenzoylaminoacetonitrile (3.9 g, 0.02 mole) was dissolved in dried ethyl acetate (60 ml) at 20° C. and treated with a few drops of a bromine solution (3.2 g, 0.02 mole) in dried ethyl acetate (10 ml). The solution was stirred until decolourised. The remainder of the bromine solution was added within 10 seconds and the solution neutralised immediately with triethylamine.

The reaction mixture was filtered to remove triethylamine hydrobromide and the filtrate was evaporated under nitrogen to leave a pale yellow solid which was washed white using a minimum of dried dichloromethane and dried under nitrogen. Yield=2.7 g=49.3%; m.p.=slow decomposition from about 80° C. onwards, sharp melting point at 123°-125° C. with frothing and decomposition.

An 'Hnmr spectrum of (IV) dissolved in alpha$^6$ acetone was complicated by impurities. However, certain discernible features were consistent with the product (IV) having the formula:

$$Cl-\text{C}_6H_4-CONHCH(CN)(Br) \quad (IV)$$

EXAMPLE 13

Conversion of the isolated bromonitrile intermediate (IV) to 4-chlorobenzoylamino(ethoxy)acetonitrile The bromonitrile (IV) (2.5 g, 0.009 mole) was dissolved in dried ethyl acetate (30 ml) at 20° C., treated with absolute ethanol (10 ml), and neutralised with triethylamine. The triethylamine hydrobromide was removed by filtration and the filtrate was treated with a decolourising carbon and filtered. The ethyl acetate was stripped off the filtrate leaving a white solid which was triturated with a methylcyclohexane/toluene mixture, filtered, and dried at 70° C. Yield=2.0 g=92% based on (IV); m.p.=109°-112° C.

I.R. and 'Hnmr spectral data were consistent with the product having the formula:

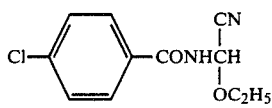

Strength (HPLC determination)=97.6%.

We claim:

1. A process for the preparation of a substituted benzamide derivative of the formula (I):

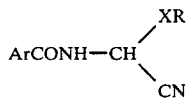

in which Ar is optionally substituted aryl; X is O, S or NH and R is optionally substituted alkyl or alkenyl when X is O of S, or is optionally substituted alkenoyl when X is NH, which comprises the steps of (a) reacting a compound of the formula (II):

with a brominating agent in ethyl acetate as a solvent, to form a compound of the formula (III):

and (b) reacting the compound (III) with a compound RXH, in which R and X have the meanings hereinbefore defined.

* * * * *

UNITED STATES PATENT AND TRADEMARK OFFICE
CERTIFICATE OF CORRECTION

PATENT NO. : 4,575,557

DATED : March 11, 1986

INVENTOR(S) : John D. Jones and David Schofield

It is certified that error appears in the above-identified patent and that said Letters Patent is hereby corrected as shown below:

Title page, in the Abstract, third line after the first formula, "alkenoyl" is changed to --alkanoyl--.

Column 1, line 59, "amine" is changed to --amide--.

Column 2, line 12, "alkenoyl" is changed to --alkanoyl--.

Column 8, line 1, "alkenoyl" is changed to --alkanoyl--.

Signed and Sealed this

Fourth Day of November, 1986

[SEAL]

Attest:

DONALD J. QUIGG

Attesting Officer

Commissioner of Patents and Trademarks